United States Patent [19]

Vieira et al.

[11] Patent Number: 5,098,477

[45] Date of Patent: Mar. 24, 1992

[54] INKS, PARTICULARLY FOR INK PRINTING

[75] Inventors: Eric Vieira; Hugh S. Laver, both of Fribourg, Switzerland

[73] Assignee: Ciba-Geigy Corporation, Ardsley, N.Y.

[21] Appl. No.: 448,179

[22] Filed: Dec. 8, 1989

[30] Foreign Application Priority Data

Dec. 14, 1988 [CH] Switzerland ............... 4624/88
Jun. 9, 1989 [CH] Switzerland ............... 2174/89

[51] Int. Cl.⁵ ............................... C09D 11/00
[52] U.S. Cl. ........................... 106/22; 106/20; 106/22; 560/64; 560/67; 514/253; 260/612
[58] Field of Search ............ 106/20, 22; 560/64; 514/253

[56] References Cited

U.S. PATENT DOCUMENTS

| | | |
|---|---|---|
| 3,584,058 | 6/1971 | Hahn . |
| 3,607,881 | 9/1971 | Izquierdo et al. ............ 514/916 |
| 3,852,305 | 12/1974 | Nagase et al. . |
| 4,025,641 | 5/1977 | Schaub et al. ............... 424/282 |
| 4,192,949 | 3/1980 | Merger et al. ................ 560/67 |
| 4,256,493 | 3/1981 | Yokoyama et al. ........... 106/22 |
| 4,501,920 | 2/1985 | Periasamy .................... 562/473 |
| 4,514,401 | 8/1982 | Tominaga et al. ............ 514/253 |

OTHER PUBLICATIONS

Derwent Abstract 88-095576/14, Japanese Sho 63-46277.
Chem. Abst. 99, 6983p.
Chem. Abst. 107, 178318a.
Derwent Abst. 19220K/05.
Derwent Abst. 87-174795/25.
Chem. Abst. 101, 25142q.
Derwent Abst. 83-335451.
Derwent Abst. 82-09446J/51.
Derwent Acc. 86-247628[38].

Primary Examiner—William R. Dixon, Jr.
Assistant Examiner—Timothy D. Saunders
Attorney, Agent, or Firm—Luther A. R. Hall

[57] ABSTRACT

Inks, particularly inks for ink jet printing, contain at least one compound of the formula I

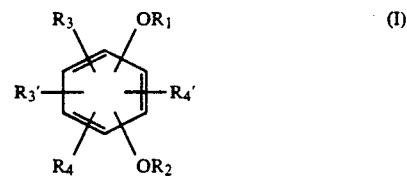

as a stabilizer. The symbols $R_1$, $R_2$, $R_3$, $R_4$, $R_3'$ and $R_4'$ are as defined in claim 1. The compounds are in part novel and are suitable for use as light stabilizers for organic materials.

9 Claims, No Drawings

INKS, PARTICULARLY FOR INK PRINTING

The present invention relates to the light-stabilization of inks, particularly inks for ink jet printing, by the addition of hydroquinone derivatives as a stabilizer, and to novel compounds and the use thereof as stabilizers.

Printing by means of ink jets is a printing process which can be controlled by electrical signals. In this process a fine jet of ink droplets is sprayed onto the recording material through a nozzle. The ink is in most cases an aqueous solution of a dye. The recording material should absorb the dye in the ink rapidly and permanently. Specially prepared papers or plastic films provided with a dye-binding layer are mostly used for this purpose. Owing to the fineness of the nozzles, pigments are hardly used, but dyes which are completely dissolved in the medium of the ink jet are mainly used. However, these dyes generally have a poorer fastness to light than the coloured pigments customary in conventional printing inks. As a result of this, the recordings prepared by ink jet printing have only a limited storage life under the action of light. If they are stored under light for a prolonged period, they begin to fade or discolour.

In order to solve this problem, it has been suggested, for example in U.S. Pat. No. 4,256,493, to add to the ink a water-soluble UV absorber of the sulfonated hydroxybenzophenone type. The metal salts of such compounds have also been suggested in JP 4 6277/88 as light stabilizing additives for inks for ink jet printing. However, benzophenone derivatives of this type and their salts have the disadvantage that they cause discolourations with certain dyes, in particular black dyes.

It has now been found that certain hydroquinone derivatives are particularly suitable for stabilizing inks, in particular inks for ink jet printing.

Dihydroxybenzene derivatives as an additive for inks for ink jet printing, are already known. Thus dihydroxybenzenes which are unsubstituted or substituted by a further —OH or —CH$_3$ group are described, for example, in JP-A 57-207,659. Gallic acid and 3,5-dimethoxy-4-hydroxybenzoic acid are also mentioned in this text. The use of dialkylhydroquinones, for example 2,5-di-t-amylhydroquinone, is known from JP-A-62-106,971. In addition, the use of the sodium salt of 2-hydroxy-4-methoxy-5-sulfobenzophenone and of 2,2′-dihydroxy-4,4′-dimethoxy-5-sulfobenzophenone is also described in this text. N-Alkanolamine salts of m-digallic acid are also described in JP-A 58-183,769 as ink additives for ink jet printing.

Hydroxybenzenes which carry 1, 2 or 3 hydroxyl groups and are unsubstituted or substituted by 1 or 2 —COOH or —COO-alkyl groups, for example tannin, gallic acid and methyl, ethyl or propyl gallate, are also described in DE-A-3,121,711. The said compounds are brought, in the form of liquid preparations, onto the carrier material as a coating in order subsequently to afford coloured complexes with solutions of transition metal salts. In this case, therefore, the hydroxy compounds are actively involved in the formation of colour and do not act as stabilizers. The carrier material coated in this manner is suitable for the ink jet printing process. There is, however, still a need for effective light stabilizers for inks.

The present invention therefore relates to an ink containing as a stabilizer at least one compound of the formula I

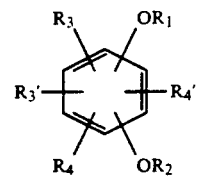

in which R$_1$ and R$_2$ independently of one another are C$_1$-C$_4$alkyl which is unsubstituted or substituted by one or 2 —OH, —COO$^\ominus$M$^\oplus$ and/or —SO$_3$$^\ominus$M$^\oplus$ groups, C$_3$-C$_5$alkenyl, C$_3$-C$_5$alkynyl,

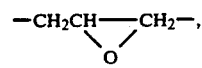

—CH$_2$CH(OH)CH$_2$—SO$_3$$^\ominus$M$^\oplus$, —CO-alkyl(C$_1$-C$_4$) which is unsubstituted or substituted by —COOR$_5$ or —CO—N(R$_5$)(R$_6$), or, if OR$_1$ and OR$_2$ are in the H$^\oplus$, a monovalent, divalent or trivalent metal cation or a group (R$_{12}$′)N$^\oplus$(R$_{12}$″)(R$_{13}$′)(R$_{14}$′), where R$_{12}$′, R$_{13}$″, R$_{13}$′ and R$_{14}$′ are independently of one another H, C$_1$-C$_4$alkyl, optionally substituted by 1 to 3 OH or optionally substituted by an O atom, allyl, cyclopentyl, cyclohexyl, phenyl, benzyl or tolyl, or R$_1$ can also be a group

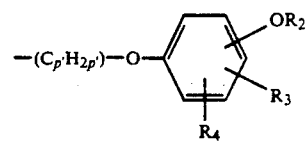

in which p′ is a number from 2 to 6, R$_5$ and R$_6$ independently of one another are H or C$_1$-C$_4$alkyl which is unsubstituted or substituted by an OH, COOR$^o$, —COO$^\ominus$M$^\oplus$, SO$_3$R$^o$ or P(O)(OR$^o$)$_2$ or P(O)(O$^\ominus$M$^\oplus$)$_2$ group, R$_3$′ and R$_4$′ independently of one another are H, C$_1$-C$_4$alkyl, OH or C$_1$-C$_4$alkoxy, R$_3$ and R$_4$ independently of one another are H, halogen, —OR$_7$, —COOR$^o$, —COO$^\ominus$M$^\oplus$, —OOC—R$_5$, —CO—N(R$_5$)(R$_6$), —(R$_5$)N—CO—R$_6$, —CO—R$_5$, —SO$_3$$^\oplus$M$^\ominus$, —SO$_2$N(R$_5$)(R$_6$), —P(OR$_5$)$_3$, —(O)-P—OR$^o$)$_2$, —(O)—P—(O$^\ominus$M$^\oplus$), C$_1$-C$_8$alkyl which is unsubstituted or substituted by 1 to 7 —OR$_5$ or —OOC—R$_5$ groups, by 1 or 2 —COOR$^o$, —COO$^\ominus$M$^\oplus$, or —CO—N(R$_5$)(R$_6$) groups or by one or two —SO$_3$$^\ominus$M$^\oplus$, —SO$_2$N(R$_5$)(R$_6$) or —(O)P—OR$^o$)$_2$, (O)P(O$^\ominus$M$^\oplus$)$_2$ groups, or allyl or C$_5$-C$_6$cycloalkyl where M$^\oplus$, R$_5$ and R$_6$ are as defined above, R$^o$ being C$_1$-C$_4$alkyl which is unsubstituted or substituted by an —OH group, and R$_7$ being C$_1$-C$_4$alkyl or —CO-alkyl(-C$_1$-C$_4$) each of which is unsubstituted or substituted by 1 or 2 —OH groups, or R$_3$ and R$_4$ independently of one another are one of the groups of the formulae II-IV

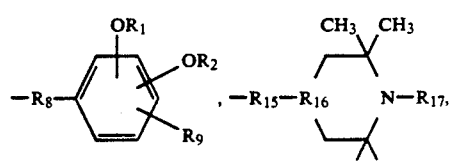

(II)        (III)

-continued

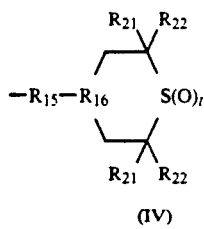

(IV)

in which $R_8$ is a direct bond, or methylene, $R_9$ is H, $C_1$-$C_8$alkyl, —COO$^\ominus$M$^\oplus$, —SO$_3^\ominus$M$^\oplus$, $R_{15}$ —CO—, —O)$_g$ $C_pH_{2p}$—CO—, —OOC—$C_pH_{2p}$—, —COO—$C_pH_{2p}$—, —O—$C_pH_{2p}$—, —CH$_2$—CH(OH)—CH$_2$— or

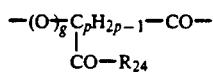

in which $R_{24}$ is —OR$_5$, —N(R$_5$)(R$_6$) or a group

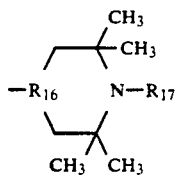

and $R_{16}$ is one of the following radicals:

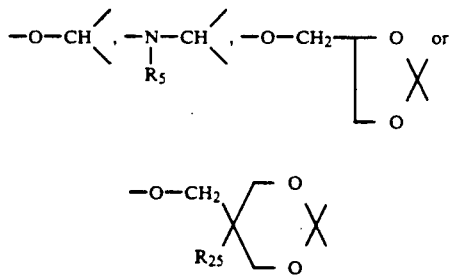

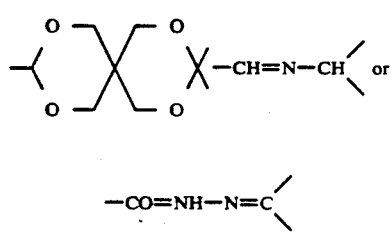

in which $R_{25}$ is H or $C_1$-$C_4$alkyl, $R_{17}$ is H, $C_1$-$C_4$alkyl which is unsubstituted or substituted by an —OH group, —CH$_2$—CH(OH)—CH$_2$—OH, $C_1$-$C_4$alkoxy, —OH, —CO-alkyl($C_1$-$C_4$), allyl, benzyl or a group

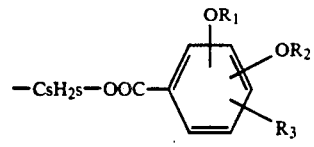

in which s is the number 2 or 3, t is a number from 0 to 2 and $R_{21}$ and $R_{22}$ independently of one another are $C_1$-$C_4$alkyl or phenyl.

Inks which should be singled out are those containing, as stabilizer, at least one compound of the formula I'

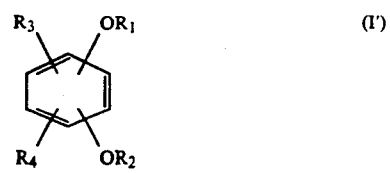

in which $R_1$ and $R_2$ independently of one another are $C_1$-$C_4$alkyl which is unsubstituted or substituted by one or 2 —OH, —COO$^\ominus$M$^\oplus$ and/or —SO$_3^\ominus$M$^\oplus$ groups, —CH$_2$CH(OH)CH$_2$—SO$_3^\ominus$M$^\oplus$ or —CO-alkyl(-$C_1$-$C_4$), M$^\oplus$ being H$^\oplus$, a monovalent, divalent or trivalent metal cation or a group (R$_{12}$')N$^\oplus$(R$_{12}$")(R$_{13}$')(R$_{14}$'), $R_5$ and $R_6$ independently of one another are H or $C_1$-$C_4$alkyl which is unsubstituted or substituted by one OH group, $R_3$ and $R_4$ independently of one another are H, halogen, —OR$_7$, —COOR$^o$, —COO$^\ominus$M$^\oplus$, —OOC—R$_5$, —CO—N(R$_5$)(R$_6$), —(R$_5$)N—CO—R$_6$, —CO—R$_5$, —SO$_3^\ominus$M$^\oplus$, —SO$_2$N(R$_5$)(R$_6$), —P(OR$_5$)$_3$, (O)P(O$^\ominus$M$^\oplus$)$_2$—(O)P—OR$^o$)$_2$, $C_1$-$C_8$alkyl which is unsubstituted or substituted by 1 to 7 —OR$_5$ or —OO-C—R$_5$ groups, by 1 or 2 —COOR$^o$, —COO$^\ominus$M$^\oplus$ or —CO—N(R$_5$)(R$_6$) groups or by an —SO$_3^\ominus$M$^\oplus$, —SO$_2$N(R$_5$)(R$_6$) or (O)P(O$^\ominus$M$^\oplus$)$_2$ —(O)P—OR$^o$)$_2$ group, R$^o$ being $C_1$-$C_4$alkyl which is unsubstituted or substituted by an —OH group, and $R_7$ being $C_1$-$C_4$alkyl which is unsubstituted or substituted by 1 or 2 —OH groups, $R_3$ and $R_4$ independently of one another are of the group of the formula II

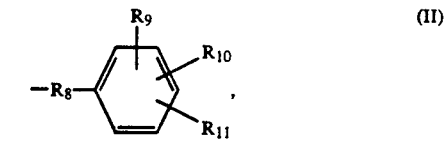

in which $R_8$ is a direct bond or methylene, $R_9$ is H, $C_1$-$C_8$alkyl, —COO$^\ominus$M$^\oplus$, or —SO$_3^\ominus$M$^\oplus$, and $R_1$ and $R_2$ are as defined above.

Inks which are also preferred are those in which $R_1$ and $R_2$ independently of one another are $C_1$-$C_4$alkyl, allyl, $C_2$-$C_4$hydroxyalkyl, —$C_1$-$C_4$-alkyl—COO$^\ominus$M$^\oplus$, —CH$_2$CH(OH)CH$_2$—SO$_3^\ominus$M$^\oplus$, or —CO-alkyl(-$C_1$-$C_4$), or in which $R_1$ is a group of the formula

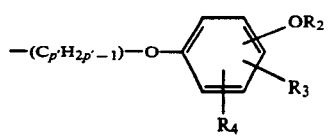

and particularly those in which $R_1$ and $R_2$ independently of one another are methyl, ethyl, allyl, —$CH_2CH_2$—OH, —$CH_2CH(OH)CH_3$, $CH_2COO^{\ominus}M^{\oplus}$ or —$CH_2CH(OH)CH_2(OH)$.

Inks of interest are those in which $R_3$ and $R_4$ independently of one another are H, halogen, —$OR_7$, —$COOR^o$, —$COO^{\ominus}M^{\oplus}$, —$CO$—$N(R_5)(R_6)$, —$SO_3^{\ominus}M^{\oplus}$, —$SO_2N(R_5)(R_6)$, $C_1$-$C_8$-alkyl which is unsubstituted or substituted by 1 or 2 —$COOR^o$ or —$COO^{\ominus}M^{\oplus}$, or allyl.

Mention should also be made of inks in which $R_3$ and/or $R_4$ are the radical —$OR_7$ in which $R_7$ is $C_1$-$C_4$alkyl, $C_2$-$C_4$hydroxyalkyl or —$CH_2$—$CH(OH)CH_2$—OH.

Preferred inks are also those in which $R_1$ and $R_2$ independently of one another are H, $C_1$-$C_4$alkyl or $C_1$-$C_4$alkyl which is substituted by carboxyl, or $R_1$ and $R_2$ together are $C_1$-$C_4$alkylene, $R_3$ and $R_4$ independently of one another are H, —$COO^{\ominus}M^{\oplus}$, $COOR^o$, $C_1$-$C_4$alkoxy, $C_1$-$C_4$alkyl—$COOR^o$, $C_1$-$C_4$alkyl—$COO^{\ominus}M^{\oplus}$, $C_1$-$C_4$alkyl or $SO_3^{\ominus}M^{\oplus}$, and $R_3'$ and $R_4'$ independently of one another are H or $C_1$-$C_4$alkoxy, and also inks in which $R_1$ and $R_2$ are $C_1$-$C_4$alkyl or hydrogen, $R_3$ is —$COOR^o$ or —$COO^{\ominus}M^{\oplus}$ and $R_4$ is methoxy.

Examples of any alkyl radicals which are $C_1$-$C_4$alkyl are methyl, ethyl, n-propyl, isopropyl, n-butyl, sec-butyl or t-butyl.

In addition to the meanings mentioned, examples of any alkyl radicals which are $C_1$-$C_8$alkyl are n-pentyl, t-amyl, n-hexyl, n-heptyl, 2-ethylhexyl, n-octyl or 1,1,3,3-tetramethylbutyl.

Examples of possible $C_1$-$C_4$hydroxyalkyl radicals are hydroxyethyl, 2-hydroxyethyl, 1-hydroxyethyl, 3-hydroxypropyl, 3-hydroxybutyl or 4-hydroxybutyl.

In addition to the meanings of $C_1$-$C_4$hydroxyalkyl, examples of possible $C_1$-$C_8$alkyl radicals which are unsubstituted or substituted by 1 to 3 OH groups are 2,3-dihydroxypropyl, 2,2-di(hydroxymethyl)-propyl, 6-hydroxyhexyl, 8-hydroxyoctyl, 1,2,4-trihydroxybut-2-yl, 1,2,6-trihydroxyhex-2-yl and 1,2,3-trihydroxyprop-2-yl.

Examples of possible $C_2$-$C_6$alkylene radicals are ethylene, ethylidene, tri-, tetra-, penta- or hexa-methylene, 1,2-propylene, 2,2-butylidene, 1,2-butylene or 2,2-dimethyl-1,3-propylene.

In addition to the preceding meanings, possible $C_1$-$C_4$alkylene radicals can also be methylene.

Possible alkylene radicals which are interrupted by one or more —O— or —$N(R_5)$— are radicals in which there are at least 2 C atoms between two hetero atoms.

Examples of possible $C_2$-$C_5$alkenyl radicals are vinyl, allyl, methallyl, propen-1-yl, buten-1-yl or penten-1-yl.

As $C_2$-$C_5$alkenyl which is substituted or unsubstituted, $R_3$ and $R_4$ can, for example, have the following formula $$-\underset{R_{29}}{\underset{|}{C}}=\underset{R_{28}}{\overset{R_{30}}{\overset{|}{C}}}$$

in which $R_{28}$ is H or $CH_3$ and $R_{29}$ and $R_{30}$ independently of one another are —$COOR^o$, —$CO$—$CH_3$, —$CON(R_5)(R_6)$ or $C\equiv N$.

As halogen, $R_3$ and $R_4$ can, for example, be Cl, Br or I.

Possible $C_5$-$C_6$cycloalkyl radicals or $C_5$-$C_7$cycloalkyl radicals can, for example, be cyclopentyl, cyclopentenyl, cyclohexyl, cyclohexenyl or cycloheptyl, preferably cyclohexyl.

Possible monovalent, divalent and trivalent metal cations can, for example, be $Na^+$ and $K^+$ and especially $Li^+$, and also $Mg^{2+}$, $Ca^{2+}$, $Zn^{2+}$, $Al^{3+}$, $Fe^{3+}$, $Cu^{2+}$, $Cr^{3+}$, $Mn^{2+}$ and $Ni^{2+}$.

In $M^{\oplus}$, substituents $R_{12}'$, $R_{12}''$, $R_{13}'$ and $R_{14}'$ are independently one another H, $C_1$-$C_4$alkyl, optionally substituted by 1 to 3 OH or optionally interrupted by an O atom, allyl, cyclopentyl, cyclohexyl, phenyl, benzyl or tolyl.

As $$HN\overset{\oplus}{\underset{R_{14}'}{\overset{R_{12}'}{-R_{13}'}}}$$

M can, for example, be $N^{\oplus}H_4$, $H N^{\oplus}(CH_3)_3$, $H N^{\oplus}(CH_2CH_3)_3$, $H_3 N^{\oplus}CH_2CH_2OH$, $H_2N^{\oplus}(CH_2CH_2OH)_2$ or $HN^{\oplus}(CH_2CH_2OH)_3$.

$X^{\ominus}$ can, for example, be $F^-$, $Cl^-$, $Br^-$, $I^-$, $R_o$—$SO_3^-$, $C_1$-$C_4$alkyl-$OSO_3^-$, $CN^-$, $SCN^-$, $OH^-$, $BF_4^-$, $PF_6^-$, $HCO_3^-$, $H_2PO_3^-$, $H_2PO_4^-$, $R_{25}$—$COO^-$, ½ $CO_3^{2-}$, ½ $SO_4^{2-}$, ½ $HPO_3^{2-}$, ½ $HPO_4^{2-}$, ½ $R_{27}$—(-$COO^-)_2$, ⅓ $PO_4^{3-}$, ⅓ $PO_3^{3-}$ or $$HO-\underset{CH_2-COO^-}{\underset{|}{\overset{CH_2-COO^-}{\overset{|}{C}}}}-COO^-$$

$R_o^o$ is unsubstituted or OH-substituted $C_1$-$C_4$alkyl $X^{\ominus}$ is preferably halide ($R^-$, $Cl^-$, $Br^-$ or $I^-$), $C_1$-$C_4$alkyl—$COO^-$, $C_1$-$C_4$alkyl-$OSO_3^-$, $CF_3$—$SO_3^-$, $CH_3$—$SO_3^-$ or $$CH_3-\!\!\!\left\langle\!\!\!\bigcirc\!\!\!\right\rangle\!\!\!-SO_3^-.$$

$X^{\ominus}$ is particularly preferably $Cl^-$, $CH_3$—$OSO_3^-$, $CH_3CH_2$—$OSO_3^-$, $CH_3SO_3^-$, $$CH_3-\!\!\!\left\langle\!\!\!\bigcirc\!\!\!\right\rangle\!\!\!-SO_3^-$$

or $CH_3$—$COO^-$.

The compounds of the formula I are in part known and some are commercially available or they can be prepared by known methods.

The inks according to the invention are distinguished by an unexpected improvement in quality. They are preferably employed in ink jet printing. In particular, their resistance to oxidation by influence of light or heat should be mentioned. In this respect, they are superior relative to corresponding recording materials which contain polyhydroxybenzene derivatives as stabilizers. These stabilizers are not efficient enough to suppress yellowing of the print. Contrary to this, the inventive inks practically do not show such yellowing. The compounds of the formula I can be employed not only in ink jet printing inks, but also in all kinds of inks, for example felt-tipped pencils, stamping pads, fountain pens, pen plotters, offset printing, letterpress printing, flexographic printing and gravure printing and also in inking ribbons for dot matrix and letter quality printing.

The inks according to the invention contain at least one dye. In this regard the nature of the ink and the dye dissolved in it and the type of printer used are immaterial.

In the printers used nowadays a distinction is drawn between those which have a continuous ink jet and "drop-on-demand" printers, in particular double-jet printers. The ink according to the invention can be used for the equipment of all these processes, specifically for printing ink jet printing paper and films.

The inks are in most cases aqueous inks, but they can also be solutions of the dye in an organic solvent or in a melted wax. In most cases aqueous inks still contain water-soluble solvents, for example mono-, di- or tri-ethylene glycols or higher ethylene glycols, propylene glycol, 1,4-butanediol or ethers of such glycols, thiodiglycol, glycerol and ethers and esters thereof, polyglycerol, mono-, di- and tri-ethanolamine, propanolamine, dimethylformamide, dimethyl sulfoxide, dimethylacetamide, N-methylpyrrolidone, 1,3-dimethylimidazolidone, methanol, ethanol, isopropanol, n-propanol, diacetone alcohol, acetone, methyl ethyl ketone or propylene carbonate.

Aqueous inks contain water-soluble dyes such as are also known for dyeing natural fibres. These can, for example, be monoazo, disazo or polyazo dyes, reactive dyes, triphenylmethane dyes, xanthene dyes or phthalocyanine dyes. Examples of these are Food Black 2, C.I. Direct Black 19, C.I. Sulphur Black 1, Acid Red 35, Acid Yellow 23 and copper phthalocyanines, and also Direct Black 38, Direct Black 168, Acid Red 249, Direct Red 227, Direct Yellow 86, Acid Blue 9, Direct Blue 86 and Direct Blue 199, Acid Red 14, Acid Red 52, Reactive Red 40, Direct Yellow 107, Direct Black 154 and Acid Red 94.

The inventive inks contain preferably at least one watersoluble azo dye.

Aqueous inks can also contain various additives in minor amounts, for example binders, surfactants, biocides, corrosion inhibitors, sequestering agents, pH buffers or conductivity additives. They can also contain other water-soluble UV absorbers or other water-soluble light stabilizers. In general, however, the addition, according to the invention, of a stabilizer of the formula I to the ink is adequate.

If the ink is a nonaqueous ink, it is a solution of the dye in an organic solvent or solvent mixture. Examples of solvents used for this purpose are alkyl carbitols, alkylcellosolves, dialkylformamides, dialkylacetamides, alcohols, especially alcohols having 1–4 C atoms, acetone, methyl ethyl ketone, diethyl ketone, methyl isobutyl ketone, diisopropyl ketone, dibutyl ketone, dioxane, ethyl butyrate, ethyl isovalerate, diethyl malonate, diethyl succinate, methyl pelargonate, butyl acetate, triethyl phosphate, ethylglycol acetate, toluene, xylene, tetralin or petroleum fractions. Examples of solid waxes as solvents, which, as an ink, must first be heated, are stearic or palmitic acid.

Inks of this type based on solvents contain dyes soluble therein, for example Solvent Red, Solvent Yellow, Solvent Orange, Solvent Blue, Solvent Green, Solvent Violet, Solvent Brown or Solvent Black. Inks of this type too can also contain further additives, such as are mentioned above for aqueous inks.

The inks according to the invention preferably contain 0.01–30% by weight, in particular 0.1–20% by weight, of a compound of the formula I or I'.

A particular problem in regard to the light-fastness of ink jet printings can occur when one ink is sprayed on top of another. The light-fastness of the printed mixed colour is often less than that of the individual inks. This problem occurs particularly if Cu phthalocyanine dyes such as Direct 86 and Direct Blue 199 are used in combination with azo dyes such as Acid Red 35, Acid Red 249 and Direct Red 227. This undesired effect can be largely suppressed by using the stabilizers of the formula I.

The compounds of the formula I or I' in the inks according to the invention are in part novel and are therefore also a subject of the present invention.

The invention also relates, therefore, to novel compounds of the formula I°

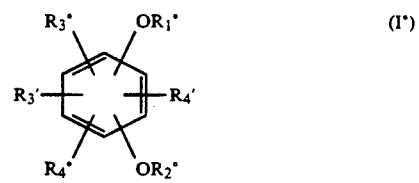 (I'°)

in which $R°_1$ and $R°_2$ independently of one another are $C_1$–$C_4$alkyl which is unsubstituted or substituted by one or 2 —OH, —COO$^\ominus$M$^\oplus$ or —SO$_3$$^\ominus$M$^\oplus$ groups, $C_3$–$C_5$alkenyl, $C_3$–$C_5$alkynyl,

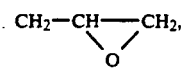

—CH$_2$CH(OH)CH$_2$—SO$_3$$^\ominus$M$^\oplus$, —CO-alkyl($C_1$–$C_4$) which is unsubstituted or substituted by —COOR$_5$ or —CO—N(R$_5$)(R$_6$) or, if OR°$_1$ and OR°$_2$ are in the ortho-position relative to one another, R°$_1$ and R°$_2$ together are $C_1$–$C_6$alkylene, M$^\oplus$ being H$^\oplus$, an alkali metal ion or a group (R$_{12}$")N$^\oplus$(R$_{12}$')(R$_{13}$')(R$_{14}$'), where R$_{12}$', R$_{13}$", R$_{13}$' and R$_{14}$' are independently of one another H, $C_1$–$C_4$alkyl, optionally substituted by 1 to 3OH or optionally interrupted by an O atom, allyl, cyclopentyl, cyclohexyl, phenyl, benzyl or tolyl, or can also be a group

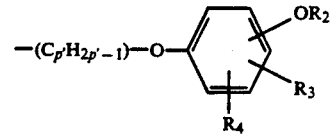

in which p' is a number from 2 to 6, R$_5$ and R$_6$ independently of one another are H or $C_1$–$C_4$alkyl which is unsubstituted or substituted by an OH, COOR°, —COO$^\ominus$M$^\oplus$, —SO$_3$$^\ominus$M$^\oplus$, or P(O)(OR°)$_2$, P(O)(O$^\ominus$M$^\oplus$)$_2$ group, R$_3$' and R$_4$' independently of one another are H, $C_1$–$C_4$alkyl, OH or $C_1$–$C_4$alkoxy, R°$_3$ and R°$_4$ independently of one another are H, halogen, —OR$_7$, —COOR°, —COO$^\ominus$M$^\oplus$, —OOC—R$_5$, —CO—N(R$_5$)(R$_6$), —(R$_5$)N—CO—R$_6$, —CO—R$_5$, —SO$_3$$^\ominus$M$^\oplus$, —SO$_2$N(R$_5$)(R$_6$), —P(OR$_5$)$_3$, —(O)-P—(OR°)$_2$, (O)P(O$^\ominus$M$^\oplus$)$_2$, ($C_1$–$C_8$alkyl which is unsubstituted or substituted by 1 to 7 —OR$_5$ or —OOC—R$_5$ groups, by 1 or 2 —COOR$^o$, —COO$^\ominus$M$^\oplus$ or —CO—N(R$_5$)(R$_6$) groups or by one —SO$_3^\ominus$M$^\oplus$, —SO$_2$N(R$_5$)(R$_6$) or —(O)P—OR$^o$)$_2$ or (O)P(O$^\ominus$M$^\oplus$)$_2$ group, allyl, or C$_5$-C$_6$cycloalkyl where M$^\oplus$, R$_5$ and R$_6$ are as definde above, R$^o$ being C$_1$-C$_4$alkyl which is unsubstituted or substituted by an —OH group, and R$_7$ being C$_1$-C$_4$alkyl or —CO-alkyl(C$_1$-C$_4$) each of which is unsubstituted or substituted by one or two —OH groups, or R$^o{}_3$ and R$^o{}_4$ independently of one another are one of the groups of the formulae II-IV

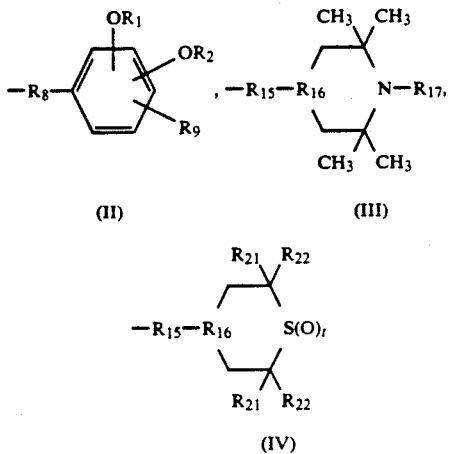

in which R$^o{}_8$ is a direct bond or methylene, R$_9$ is H, C$_1$-C$_8$alkyl, —COO$^\ominus$M$^\oplus$ or —SO$_3^\ominus$M$^\oplus$, R$_{15}$ —CO—, —O)$_g$C$_p$H$_{2p}$—CO—, —OOC—C$_p$H$_{2p}$—, —COO—C$_p$H$_{2p}$—, —O—C$_p$H$_{2p}$—, —CH$_2$—CH(OH)—CH$_2$— or

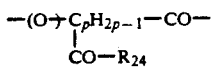

in which R$_{24}$ is —OR$_5$, —N(R$_5$)(R$_6$) or a group

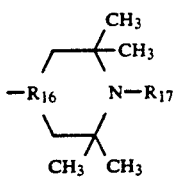

and R$_{16}$ is one of the following radicals:

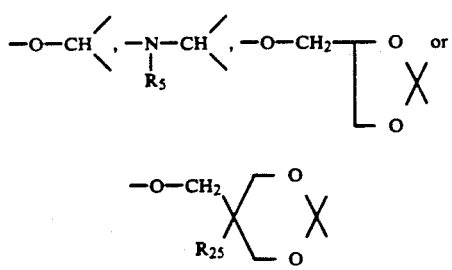

in which R$_{25}$ is H or C$_1$-C$_4$alkyl,

R$_{17}$ is H, C$_1$-C$_4$alkyl which is unsubstituted or substituted by an —OH group, —CH$_2$—CH(OH)—CH$_2$—OH, C$_1$-C$_4$-alkoxy, —OH—, —CO-alkyl(C$_1$-C$_4$), allyl, benzyl or a group

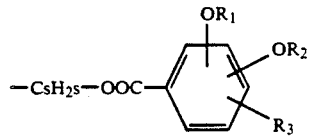

in which s is the number 2 or 3, t is a number from 0 to 2 and R$_{21}$ and R$_{22}$ independently of one another are C$_1$-C$_4$alkyl or phenyl.

The possible meanings for R$^o{}_1$, R$^o{}_2$, R$^o{}_3$ and R$^o{}_4$ already given above under the formula I or I' as examples are also applicable here.

Preferred compounds of the formula I$^o$ are those in which R$^o{}_1$ and R$^o{}_2$ independently of one another are C$_1$-C$_4$alkyl which is substituted by an —OH group, —CH$_2$—CH(OH)CH$_2$—SO$_3^\ominus$M$^\oplus$, —C$_1$-C$_4$alkyl-COO$^\ominus$M$^\oplus$ or —CO-alkyl(C$_1$-C$_4$) which is unsubstituted or substituted by —COOR$_5$, —CO—N(R$_5$)(R$_6$) or by 1 or 2OH groups.

Furthermore, recording materials of interest are those in which R$_3$ and/or R$_4$ are the radical —OR$_7$, R$_7$ being C$_1$-C$_4$alkyl, C$_2$-C$_4$hydroxyalkyl or —CH$_2$—CH(OH)CH$_2$—OH.

Compounds which are also preferred are those in which R$^o{}_4$ is hydrogen and R$^o{}_3$ is —SO$_3^\ominus$M$^\oplus$, —COOR$_5$ or —CO—NHR$_5$.

As already described, the novel compounds of the formula I$^o$ can be prepared by methods known per se.

The novel compounds of the formula I$^o$ are used as stabilizers for organic materials, in particular against damage thereto by light. The materials to be stabilized can, for example, be oils, fats, gelatines, waxes, cosmetics, dyes or polymers.

The use of compounds of the formula I$^o$ as stabilizers for organic polymers and for gelatine emulsions containing dyes in photographic materials is preferred.

The invention also relates to compositions containing an organic material and at least one compound of the formula I$^o$ as a stabilizer.

The following are examples of polymers which can be stabilized advantageously by means of the compounds, according to the invention, of the formula I$^o$:

1. Polymers of monoolefins and diolefins, for example polypropylene, polyisobutylene, polybut-1-ene, polymethylpent-1-ene, polyisoprene or polybutadiene, and polymers of cycloolefins, for example cyclopentene or norbornene; and also polyethylene (which can, if desired, be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene or of polypropylene with polyethylene (for example PP/HDPE or PP/LDPE) and mixtures of different types of polyethylene (for example LDPE/HDPE).

3. Copolymers of monoolefins and diolefins with one another or with other vinyl monomers, for example ethylene/propylene copolymers, linear low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1, for example polypropylene-ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$), including hydrogenated modifications thereof (for example tackifying resins).

4. Polystyrene, poly-(p-methylstyrene) and poly-($\alpha$-methylstyrene).

5. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/maleic anhydride or styrene/acrylonitrile/methyl acrylate; mixtures of high impact resistance formed from styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene or $\alpha$-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene, styrene and maleimide on polybutadiene, styrene and alkyl acrylates or alkyl methacrylates on polybutadiene, styrene and acrylonitrile on ethylene/propylene/diene/terpolymers, styrene and acrylonitrile on polyalkyl acrylates or polyalkyl methacrylates, styrene and acrylonitrile on acrylate/butadiene copolymers and mixtures thereof with the copolymers mentioned under 5), such as are known, for example, as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, in particular polymers formed from halogen-containing vinyl compounds, for example polyvinyl chloride, polyvinylidene chloride, polyvinyl fluoride or polyvinylidene fluoride; and copolymers thereof, such as vinyl chloride/vinylidene chloride, vinyl chloride/vinyl acetate or vinylidene chloride/vinyl acetate.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned under 8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, stearate, benzoate or maleate, polyvinylbutyral, polyallyl phthalate or polyallylmelamine; and copolymers thereof with olefins mentioned in item 1.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene, and also those polyoxymethylenes containing comonomers, for example ethylene oxide, and polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters and polybutadienes having terminal hydroxyl groups on the one hand and from aliphatic or aromatic polyisocyanates on the other hand, and also precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 or 4/6, polyamide 11, polyamide 12 and aromatic polyamides formed from m-xylene, a diamine and adipic acid; and polyamides prepared from hexamethylenediamine and isophthalic and/or terephthalic acid and, if appropriate, an elastomer as modifier, for example poly-2,4,4-trimethylhexamethyleneterephthalamide or poly-m-phenyleneisophthalamide. Block copolymers of the polyamides mentioned above with polyolefins, olefin copolymers, ionomers or chemically attached or grafted elastomers; or with polyethers, for example polyethylene glycol, polypropylene glycol or polytetramethylene glycol. Also polyamides or copolyamides modified with EPDM or ABS; and polyamides which have been condensed during processing ("RIM polyamide systems").

16. Polyureas, polyimides, polyamide-imides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates and block polyether-esters derived from polyethers having hydroxyl end groups; and also polyesters modified with polycarbonates or MBS.

18. Polycarbonates and polyester-carbonates.

19. Polysulfones, polyether-sulfones and polyether-ketones.

20. Crosslinked polymers derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins derived from copolyesters of saturated and unsaturated dicarboxylic acids with polyhydric alcohols, and also vinyl compounds as crosslinking agents, and also halogen-containing modifications thereof of low flammability.

23. Crosslinkable acrylic resins derived from substituted acrylic acid esters, for example from epoxyacrylates, urethane-acrylates or polyester-acrylates.

24. Alkyd resins, polyester resins and acrylate resins crosslinked with melamine resins, urea resins, polyisocyanates or epoxy resins.

25. Crosslinked epoxy resins derived from polyepoxides, for example from bis-glycidyl ethers or cycloaliphatic diepoxides.

26. Natural polymers, such as cellulose, natural rubber, gelatine and their polymer-homologously chemically modified derivatives, such as cellulose acetates, propionates and butyrates or the cellulose ethers, such as methylcellulose; and also colophony resins and derivatives.

27. Mixtures (polyblends) of the abovementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP and PA/PPO.

28. Natural and synthetic organic substances which are pure monomeric compounds or mixtures of such, for example mineral oils, animal or vegetable fats, oils and waxes, or oils, waxes and fats based on synthetic esters (for example phthalates, adipates, phosphates or trimellitates), and mixtures of synthetic esters with mineral oils in any desired weight ratios, such as are used, for example, as spin finishes, and aqueous emulsions thereof.

29. Aqueous emulsions of natural or synthetic rubbers, for example natural rubber latex or latices of carboxylated styrene/butadiene copolymers.

In regard to their use in gelatine, it should be stated that the stabilizers according to the invention can be present in all photographic materials which contain a dye or dye precursor, for example a colour coupler, in gelatine emulsions, such as photographic silver dye bleach, chromogenic and transfer materials.

The stabilizers according to the invention are advantageously added to the polymers in a concentration of 0.01–10% by weight, calculated on the material to be stabilized. It is preferable to incorporate into the material to be stabilized 0.05 to 5.0% by weight, particularly preferably 0.1 to 2.0% by weight, of the compounds of the formula I°, calculated based on the former.

The incorporation can, for example, be effected by mixing in the stabilizers according to the invention and, if appropriate, further additives by the methods customary in the industry, before or during shaping, or by applying the dissolved or dispersed compounds to the polymer, if appropriate with subsequent evaporation of the solvent. The stabilizers according to the invention can also be added to the plastics to be stabilized in the form of a master-batch containing the stabilizer in a concentration of, for example, 2.5 to 25% by weight.

The compounds of the formula I° can also be added before or during the polymerization or crosslinking reaction. Polymers which are stabilized without further treatment are obtained in this way.

The materials thus stabilized can be used in a very wide variety of shapes, for example as films, fibres, tapes, moulding materials or profiles or as binders for paints, adhesives or cements.

In practice, the stabilizers according to the invention can be employed together with other stabilizers.

The following should be mentioned as examples of other additives which can be employed together with the stabilizers used in accordance with the invention:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol and 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone and 2,6-diphenyl-4-octadecyloxyphenol.

1.3. Hydroxylated thiodiphenyl ethers, for example 2,2'-thiobis-(6-tert-butyl-4-methylphenol), 2,2'-thiobis-(4-octylphenol), 4,4'-thiobis-(6-tert-butyl-3-methylphenol), 4,4'-thiobis-(6-tert-butyl-2-methylphenol).

1.4. Alkylidene bisphenols, for example 2,2'-methylenebis-(6-tert-butyl-4-methylphenol), 2,2'-methylenebis-(6-tert-butyl-4-ethylphenol), 2,2'-methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-di-tert-butylphenol), 2,2'-ethylidenebis-(4,6-di-tert-butylphenol), 2,2'-ethylidenebis-(6-tert-butyl-4-isobutylphenol), 2,2'-methylenebis-[6-(α-methylbenzyl)-4-nonylphenol], 2,2'-methylenebis-[6-(α,α-dimethylbenzyl)-4-nonylphenol], 4,4'-methylenebis-(2,6-di-tert-butylphenol), 4,4'-methylenebis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene and bis-[2-(3'-tert-butyl-2'-hydroxy-5'-methylbenzyl)-6-tert-butyl-4-methylphenyl]terephthalate.

1.5. Benzyl compounds, for example 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzylmercaptoacetate, bis-(4-tert-butyl-3-hydroxy-2,6-dimethylbenzyl)-dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxybenzylphosphonate, the Ca salt of monoethyl 3,5-di-tert-butyl-4-hydroxybenzylphosphonate and 1,3,5-tris-(3,5-dicyclohexyl-4-hydroxybenzyl)isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine and octyl N-(3,5-di-tert-butyl-4-hydroxyphenyl)-carbamate.

1.7. Esters of β-(3,5-di-tert-butyl-4-hydroxyphenyl)-propionic acid, with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxyethyl)oxamide.

1.8. Esters of β-(5-tert-butyl-4-hydroxy-3-methylphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxyethyl)oxamide.

1.9. Esters of β-(3,5-dicyclohexyl-4-hydroxyphenyl)-propionic acid with monohydric or polyhydric alcohols, for example with methanol, octadecanol, 1,6-hexanediol, neopentyl glycol, thiodiethylene glycol, diethylene glycol, triethylene glycol, pentaerythritol, tris-(hydroxyethyl)isocyanurate and N,N'-bis-(hydroxyethyl)oxamide.

1.10. Amides of β-(3,5-di-tert-butyl-4-hydroxyphenyl)-propionic acid, for example, N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

2. UV absorbers and light stabilizers 2.1. 2-(2'-Hydroxyphenyl)-benzotriazoles, for example the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, 3',5'-di-tert-amyl-, 3',5'-bis-(α,α-dimethylbenzyl)-derivative.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy- derivative.

2.3. Esters of substituted or unsubstituted benzoic acids, for example 4-tert-butylphenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

2.5. Nickel compounds, for example nickel complexes of 2,2'-thiobis-[4-(1,1,3,3-tetramethylbutyl)-phenol], such as the 1:1-complex or the 1:2 complex, if appropriate with additional ligands, such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as the methyl or ethyl ester, nickel complexes of ketoximes, such as 2-hydroxy-4-methylphenyl undecyl ketoxime, or nickel complexes of 1-phenyl-4-lauroyl-5-hydroxypyrazole, if appropriate with additional ligands.

2.6. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product formed from 1-hydroxyethyl-2,2,6,6-tetramethyl-4-hydroxypiperidine and succinic acid, the condensation product formed from N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate or 1,1'-(1,2-ethanediyl)-bis-(3,3,5,5-tetramethyl-piperazinone), 1,2,2,6,6-pentamethylpiperidin-4-ol, 2,2,6,6-tetramethylpiperidin-4-ol.

2.7. Oxamides, for example 4,4'-di-octyloxyoxanilide, 2,2'-di-octyloxy-5,5'-di-tert-butyloxanilide, 2,2'-didodecyloxy-5,5'-di-tert-butyloxanilide, 2-ethoxy-2'-ethyloxanilide, N,N'-bis-(3-dimethylaminopropyl)-oxamide, 2-ethoxy-5-tert-butyl-2'-ethyloxanilide and a mixture thereof with 2-ethoxy-2'-ethyl-5,4'-di-tert-butyloxanilide or mixtures of o-methoxy- and p-methoxy-disubstituted oxanilides and of o-ethoxy- and p-ethoxy-disubstituted oxanilides.

2.8. 2-(2-Hydroxyphenyl)-1,3,5-triazines, for example 2,4,6-tris-(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis-(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine or 2-(2-hydroxy-4-dodecyloxyphenyl)-4,6-bis-(2,4-dimethylphenyl)-1,3,5-triazine.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, tristearyl sorbitol triphosphite, tetrakis-(2,4-di-tert-butylphenyl) 4,4'-biphenylenediphosphonite and 3,9-bis-(2,4-di-tert-butylphenoxy)-2,4,8,10-tetraoxa-3,9-diphosphaspiro[5.5]undecane.

5. Compounds which destroy peroxides, for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythrityl tetrakis-(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali and alkaline earth metal salts of higher fatty acids, for example Ca stearate, Zn stearate, Mg stearate, Na ricinoleate and K palmitate, antimony pyrocatecholate or tin pyrocatecholate.

8. Nucleating agents, for example 4-tert-butylbenzoic acid, adipic acid or diphenylacetic acid.

9. Fillers and reinforcing agents, for example calcium carbonate, silicates, glass fibres, asbestos, talc, kaolin, mica, barium sulfate, metal oxides and hydroxides, carbon black or graphite.

10. Other additives, for example plasticizers, lubricants, emulsifiers, pigments, fluorescent brighteners, fire-retarding agents, antistatic agents or blowing agents.

The compounds of the formula I can be prepared by processes known from the literature. The starting materials are, for example, polyhydroxybenzenes, such as catechol, resorcinol, hydroquinone and pyrogallol derivatives. These can be carboxylated, for example by reacting the corresponding phenates with $CO_2$, or this stage is achieved by formylation and subsequent oxidation. Sulfonation with sulfuric acid or chlorosulfonic acid permits the introduction of sulfonic acid groups into the benzene ring. Carboxyalkyl groups can be introduced by alkylating the phenolic hydroxyl groups, by using halogenocarboxylic acid esters, such as methyl chloroacetate, ethyl bromoacetate or methyl 3-bromopropionate, and also by means of olefinic alkylating agents, such as methyl or ethyl (meth)acrylate, dimethyl maleate or fumarate, maleic or itaconic anhydride and the like, or by means of epoxy compounds, such as methyl 2,3-epoxypropionate or dimethyl 2,3-epoxysuccinate, and hydrolysis of the ester function. The use of halogenalkanesulfonic, epoxyalkanesulfonic or olefin-alkanesulfonic acid derivatives, such as 3-bromo-2-hydroxypropanesulfonic acid, 3-chloropropanesulfonic acid, 2,3-epoxypropanesulfonic acid, an alkanesulfonic acid, a dimethylalkanesulfonic acid or sulfonic acid lactones such as 1,3-propylene sulfone, permits sulfonyl groups to be introduced directly. Allyl substituents can be attached directly to the benzene ring via the Claisen rearrangement of the corresponding allyl ethers. Further functional groups can then be added on to the double bond contained therein, for example by sulfonation, halogenation or epoxidation followed by reaction with sodium sulfite or trialkyl phosphites, which is equivalent to a direct introduction of a sulfo or phosphoric acid group. The phenolic hydroxyl groups can be alkylated by means of a large number of alkylating agents, for example alkyl, alkenyl or alkinyl halides, dialkyl sulfates or alkylphosphonic acid esters, that is to say, for example, by means of methyl iodide, ethyl bromide, propyl or butyl chloride, dimethyl and diethyl sulfate, an alkyl bromide, a dimethylalkyl bromide, propargyl bromide and the like. Quaternary ammonium groups can be obtained by quaternizing amines by using the abovementioned alkylating agents. Alkoxy groups can be introduced by halogenation and substituting the halogen atom with an alcoholate. Monocarboxylic and polycarboxylic acid derivatives can be prepared, for example, by metallating the corresponding monoalkoxybenzenes or polyalkoxybenzenes with, for example, an alkyllithium or a Grignard reagent and subsequently reacting the product with $CO_2$.

The following examples illustrate the invention further. Percentages are by weight unless stated otherwise.

EXAMPLE 1

A coating composition based on silica/polyvinyl alcohol/mordant is prepared from the following components: 14.2 g of a 10% solution of polyvinyl alcohol (Riedel de Haen GmbH), 0.02 g of di-t-octylphenolpolyethylene oxide, 2.00 g of silica (Sylord ® type 244, Grace and Co.), 0.4 g of Polyfix ® 601 (mordant made by Showa High Polymer Co.) and 11 g of water.

The resulting coating composition is dispersed by means of ultrasonic sound and is filtered through a sieve composed of polyester fibres and having a mesh width of 24 μm. The pH is adjusted to 7.0 by adding 2N sodium hydroxide solution.

The coating compositions are applied to photographic paper in a thickness of 50 μm by means of a wire spiral. The coating obtained after drying with warm air has a dry weight of about 5.0 g/m$^2$.

The recording material is printed in each case with an ink according to the invention which contains a stabilizer of the formula I or is without stabilizer as a blank sample.

The inks for this purpose can, for example, be prepared as follows: 6 g of a stabilizer of the formula I are dissolved in a mixture of 47 g of diethylene glycol and 47 g of water, and the pH of this solution is adjusted to a value of, preferably, 7.0 with a base, for example lithium hydroxide. Further solutions, each containing 6 g of a dye (C.I. Acid Yellow 23, C.I. Acid Red 249 or C.I. Food Black 2), in 47 g of diethylene glycol and 47 g of water are prepared. The solutions are filtered through an ultrafilter of pore width 0.3 μm. The printing inks according to the invention are then obtained by mixing the stabilizer solutions with the dye solutions in equal amounts.

The resulting printing inks consist of: 3% of dye, 3% of stabilizer of the formula I, 47% of diethylene glycol and 47% of water.

Each of the blank samples is prepared using identical amounts of a dye solution and a mixture of 1 part of diethylene glycol and 1 part of water.

The inks are filled into the ink cartridges of the "think-jet" (Hewlett-Packard) ink jet printing apparatus. Printed samples having a dot density of 192×96 dots per inch$^2$ are produced.

After storing for one week in order to dry the inks completely, the ink density (intensity) of the printed samples is determined by means of a densitometer (Macbeth TR 924) using a Status A filter. The sample prints are then irradiated in an Atlas weather-O-meter using a xenon lamp having a luminous intensity of 81 klux behind a filter made of window glass 6 mm thick. The ink density is then measured again, in order to determine the percentage loss of colour density.

The results are summarized in Table 1 below. Lower values mean higher fastness to light.

TABLE 1

| | | LOSS OF COLOUR DENSITY (%) | | |
|---|---|---|---|---|
| SAMPLE | STABILIZER | Acid Yellow 23 5 kJ/cm$^2$* | Acid Red 249 10 kJ/cm$^2$* | Food Black 2 45 kJ/cm$^2$* |
| 1 | — | 53 | 84 | 31 |
| 2 | 2,3-Dimethoxybenzoic acid | 37 | 73 | 21 |

*Amount of radiation energy within the 300–800 nm range measured.

EXAMPLE 2

The effectiveness as stabilizers for printing inks of further compounds of the formula I is tested as described in Example 1. The compounds indicated below also produce a considerable reduction in the loss of colour density. The following compounds are involved (acids and corresponding salts): 3,4-dimethoxybenzoic acid, 3,5-dimethoxy-4-hydroxybenzoic acid, 1,3-dimethoxy-2-hydroxybenzene, 2,5-dimethoxybenzoic acid, 3,4-dimethoxybenzenesulfonic acid, 3,4,5-trimethoxyphthalic acid, 4,5-dimethoxyphthalic acid, 2,3-bis-(carboxymethyloxy)benzoic acid, 3,4-methylenedioxybenzoic acid, 2,3-ethylenedioxybenzoic acid, 2,3-isopropylidenedioxybenzoic acid, methyl 3,4-dihydroxybenzoate, 2,5-dimethoxybenzoic acid, 3,5-dimethoxybenzoic acid, 2,6-dimethoxybenzoic acid, 1,3-dimethoxy-2-hydroxybenzene, 1,2,3-trimethoxybenzoic acid, 2,4,5-trimethoxybenzoic acid, 3,4,5-trimethoxybenzoic acid, methyl 3,4-dihydroxybenzoate, 1,4-dihydroxy-2-methylbenzene, 2,5-dihydroxyphenylacetic acid, 1,4-bis(carboxymethyl)-2,5-dihydroxybenzene and the compounds of the following formulae:

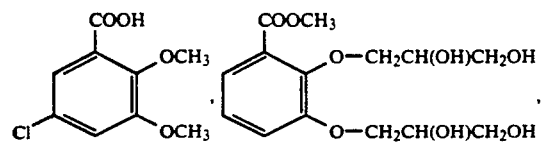

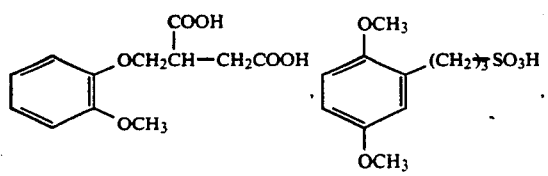

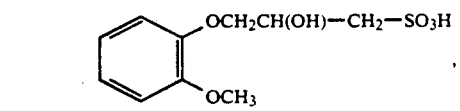

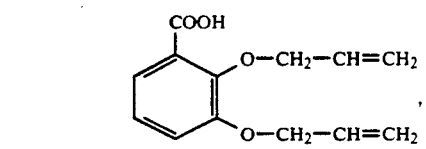

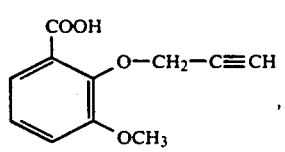

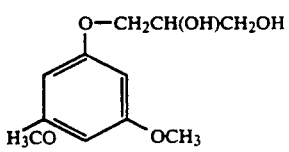

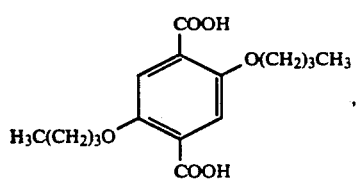

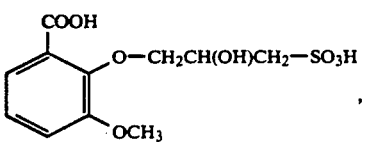

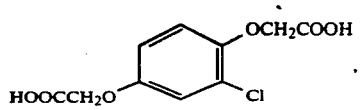

-continued

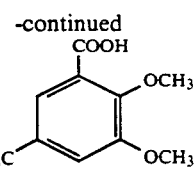

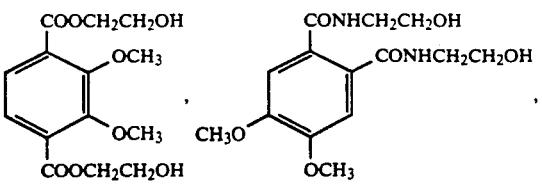

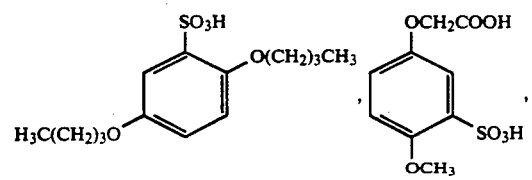

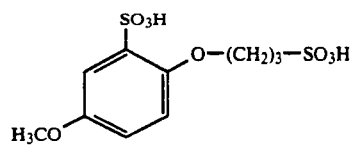

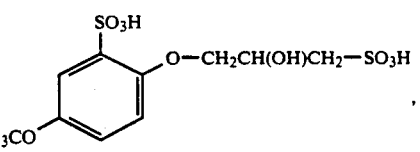

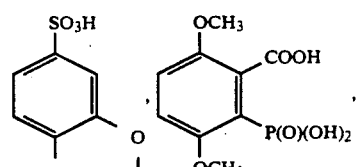

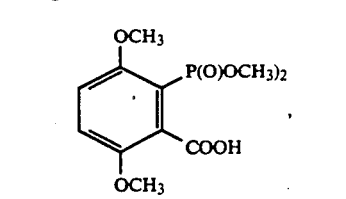

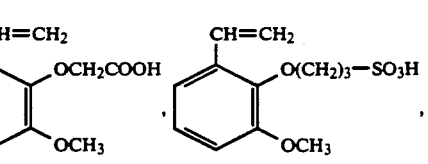

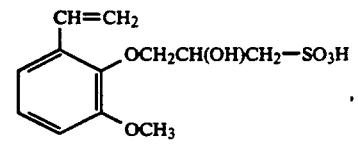

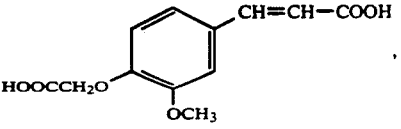

-continued

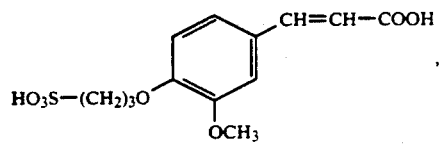

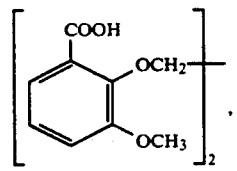

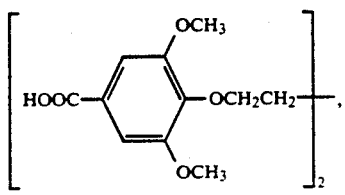

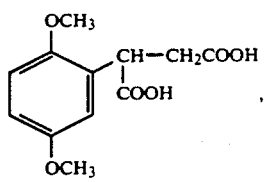

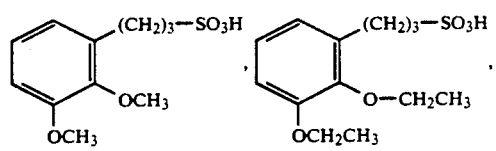

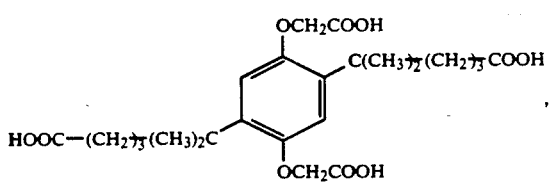

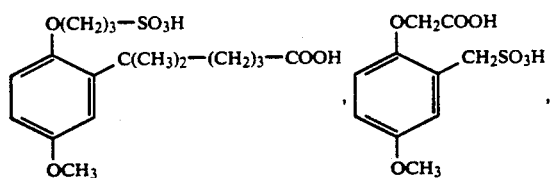

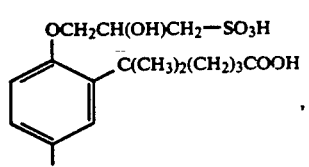

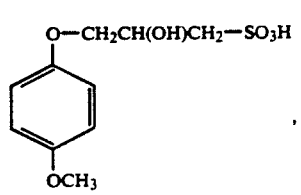

-continued

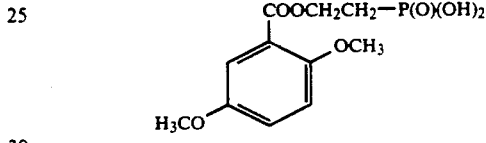

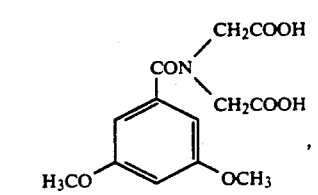

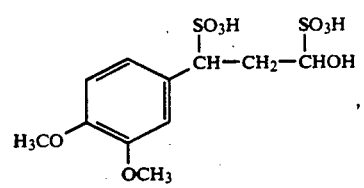

EXAMPLE 3

Ink jet printing inks are prepared from 3 g in each case of a dye (C.I. Acid Yellow 23, C.I. Acid Red 35, C.I. Direct Red 227, C.I. Acid Red 249 and C.I. Food Black 2), 10 g of a stabilizer of the formula I, 43.5 g of diethylene glycol and 43.5 g of water. The solutions are filtered through an ultrafilter of pore width 0.3 μm and are filled into the ink cartridges of the "Quiet-Jet" (Hewlett-Packard) ink jet printing apparatus. Printed samples having a dot density of 192×96 dots per $inch^2$ are prepared with the inks according to the invention on "Paint-Jet" ink jet printing paper (Hewlett-Packard). The inks are completely dry after being stored for one week. The colour densities of the inks are measured analogously to Example 1. The results are summarized in Table 2. As before, lower values mean higher fastness to light.

TABLE 2

| Sample | Stabilizer | Loss of colour density (%) | | | | |
|---|---|---|---|---|---|---|
| | | Acid Yellow 23 10 kJ/cm² | Acid Red 35 10 kJ/cm² | Direct Red 227 10 kJ/cm² | Acid Red 249 10 kJ/cm² | Food Black 2 60 kJ/cm² |
| 1 | — | 40 | 53 | 72 | 64 | 69 |
| 2 | 2,3-Dimethoxybenzoic acid [lithium salt] | 21 | 40 | 65 | 45 | 68 |
| 3 | 3,4-Dimethoxybenzoic acid [lithium salt] | 20 | 43 | 63 | 53 | 67 |
| 4 | 2,6-Dimethoxybenzoic acid [lithium salt] | 21 | 42 | 59 | 52 | 66 |
| 5 | 3,4,5-Trimethoxybenzoic acid [lithium salt] | 22 | 42 | 60 | 43 | 63 |

EXAMPLE 4

Fluorescent inks are prepared from 1 g in each case of a dye (cyanosin, Na fluorescein and rhodamine 6G), 8 g of water, 2 g of N,N-dimethylimidazolidone, 1 g of glycerol and 2 g of a stabilizer of the formula I. 2 g of water are used in addition instead of the stabilizer in the blank sample. The inks according to the invention are filled into felt tip recorders (0.7 mm, for Hewlett-Packard pen plotters) made by Faber Castell, which have been washed out and dried. Coloured test samples are produced on Hewlett-Packard non-glossy plotter paper at a recording speed of 20 cm/second and a line interval of 12 lines per cm. After drying for one week, the colour densities of the samples are measured as in Example 1. The results are summarized in Table 3.

TABLE 3

| Sample | Stabilizer | Loss of colour density at 5 kJ/cm² (%) | | |
|---|---|---|---|---|
| | | Na fluoresceine | Cyanosin | Rhodamine 6G |
| 1 | — | 70 | 93 | 77 |
| 2 | 3,4,5-Trimethoxybenzoic acid Lithium salt | 47 | 84 | 77 |
| 3 | 2,3-Dimethoxybenzoic acid Lithium salt | 45 | 88 | 63 |

EXAMPLE 5

Non-fluorescent pen plotter inks are prepared from in each case 1 g of a dye (C.I. Acid Red 35 and C.I. Acid Red 249), 9 g of water, 1 g of glycerol and 2 of a stabilizer of the formula I. These inks are filled into felt tip recorders analogously to Example 4. They are used to produce test prints on plotter paper. The colour densities of the samples are measured as in Example 1. The results are summarized in Table 4.

TABLE 4

| Sample | Stabilizer | Loss of colour density at 5 kJ/cm² (%) | |
|---|---|---|---|
| | | Acid Red 35 | Acid Red 249 |
| 1 | — | 27 | 62 |
| 2 | 3,4,5-Trimethoxybenzoic acid lithium salt | 16 | 29 |
| 3 | 2,3-Dimethoxybenzoic acid lithium salt | 17 | 21 |

What is claimed is:

1. An ink containing as stabilizer at least one compound of formula I

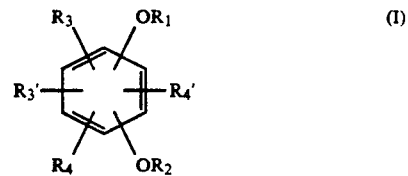

in which $R_1$ and $R_2$ independently of one another are $C_1$-$C_4$alkyl which is unsubstituted or substituted by one or two —OH or —COO$^-$M$^+$ groups; $C_3$-$C_5$alkenyl or $C_3$-$C_5$alkynyl;

M$^+$ is H$^+$ or a monovalent, divalent of trivalent metal cation, $R'_3$ and $R'_4$ independently of one another are H, $C_1$-$C_4$-alkyl, OH or $C_1$-$C_4$alkoxy, $R_3$ and $R_4$ independently of one another are H, —OR$_7$, —COO$^-$M$^+$, $C_1$-$C_8$alkyl which is unsubstituted or substituted by 1 or 2 —OR$_5$ or —COO$^-$M$^+$ groups; or allyl;

$R_5$ is hydrogen or $C_1$-$C_4$alkyl which is unsubstituted or substituted by an OH or —COO$^-$M$^+$ group, and $R_7$ is $C_1$-$C_4$alkyl or allyl.

2. An ink according to claim 1, containing, as the stabilizer, at least one compound of the formula I'

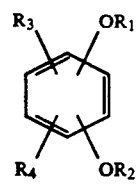

in which $R_1$ and $R_2$ independently of one another are $C_1$-$C_4$alkyl which is unsubstituted or substituted by one or 2 —OH or —COO$^\ominus$M$^\oplus$ groups, M$^\oplus$ being H$^\oplus$, a monovalent, divalent or trivalent metal cation, $R_5$ is H or $C_1$-$C_4$alkyl which is unsubstituted or substituted by one OH group, $R_3$ and $R_4$ independently of one another are H, —OR$_7$, —COO$^\ominus$M$^\oplus$, —(O)P—OR$^o$)$_2$, $C_1$-$C_8$alkyl which is unsubstituted or substituted by 1 or 2 $OR_5$, by 1 or 2 $-COO^\ominus M^\oplus$ groups, and $R_7$ being $C_1-C_4$alkyl which is unsubstituted or substituted by 1 or 2 —OH groups.

3. An ink according to claim 1, wherein $R_1$ and $R_2$ independently of one another are $C_1-C_4$alkyl, allyl, $C_2-C_4$hydroxyalkyl or $-C_1-C_4$-alkyl-$COO^\ominus M^\oplus$.

4. An ink according to claim 3, wherein $R_1$ and $R_2$ independently of one another are methyl, ethyl, allyl, $-CH_2CH_2-OH$, $CH_2COO^\ominus M^\oplus$, $-CH_2CH(OH)CH_3$ or $-CH_2CH(OH)CH_2(OH)$.

5. An ink according to claim 1, wherein $R_3$ and $R_4$ independently of one another are H, $-OR_7$, $-COOR^o$, $-COO^\ominus M^\oplus$, $C_1-C_8$-alkyl which is unsubstituted or substituted by 1 or 2 $-COO^\ominus M^\oplus$, or allyl.

6. An ink according to claim 1, wherein $R_3$ and $R_4$ are independently the radical $-OR_7$ in which $R_7$ is $C_1-C_4$alkyl, $C_2-C_4$hydroxyalkyl or $-CH_2-CH(OH)CH_2-OH$.

7. An ink according to claim 1, wherein $R_1$ and $R_2$ independently of one another are $C_1-C_4$alkyl or $C_1-C_4$alkyl which is substituted by carboxyl, $R_3$ and $R_4$ independently of one another are H, $-COO^\ominus M^\oplus$, $C_1-C_4$alkoxy, $C_1-C_4$alkyl-$COO^\ominus M^\oplus$ or, and $R_3'$ and $R_4'$ independently of one another are H or $C_1-C_4$alkoxy.

8. An ink according to claim 1, wherein $R_1$ and $R_2$ are $CH_3$, $R_3$ is $-COO^\ominus M^\oplus$ and $R_4$ is methoxy.

9. An ink according to claim 1 which contains, as the stabilizer, lithium 3,4,5-trimethoxybenzoate.

* * * * *